(12) United States Patent
Buzot

(10) Patent No.: US 6,582,389 B2
(45) Date of Patent: Jun. 24, 2003

(54) APPLICATOR FOR DELIVERING BULKY DEVICES

(75) Inventor: Herve Buzot, North Brunswick, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 66 days.

(21) Appl. No.: 09/742,688

(22) Filed: Dec. 20, 2000

(65) Prior Publication Data

US 2002/0111578 A1 Aug. 15, 2002

(51) Int. Cl.⁷ ................................................. A61F 13/20
(52) U.S. Cl. ........................................... 604/15; 604/11
(58) Field of Search .................... 604/11–18, 285–288, 604/311, 57, 59, 60

(56) References Cited

U.S. PATENT DOCUMENTS

| | | | |
|---|---|---|---|
| 1,969,671 A | | 8/1934 | Nelson |
| 2,351,836 A | | 6/1944 | Popper |
| 4,048,998 A | | 9/1977 | Nigro |
| 4,273,125 A | * | 6/1981 | Sakurai |
| 4,276,881 A | * | 7/1981 | Lilaonitkul |
| 4,286,594 A | | 9/1981 | Cunningham |
| 4,286,595 A | * | 9/1981 | Ring |
| 4,318,404 A | | 3/1982 | Cunningham |
| 4,479,791 A | * | 10/1984 | Sprague |
| 4,508,531 A | | 4/1985 | Whitehead |
| 4,676,773 A | * | 6/1987 | Sheldon |
| 4,755,164 A | | 7/1988 | Hinzmann |
| 4,923,440 A | | 5/1990 | Genaro |
| 5,087,239 A | | 2/1992 | Beastall et al. |
| 5,279,541 A | | 1/1994 | Frayman et al. |
| 5,346,468 A | | 9/1994 | Campion et al. |
| 5,348,534 A | | 9/1994 | Tomaszewski et al. |
| 5,569,177 A | | 10/1996 | Fox et al. |
| 5,599,293 A | | 2/1997 | Orenga et al. |
| 5,693,009 A | | 12/1997 | Fox et al. |
| 5,817,121 A | | 10/1998 | Christoudias |
| 5,910,520 A | | 6/1999 | Dabi et al. |
| 6,095,998 A | | 8/2000 | Osborn, III et al. |

FOREIGN PATENT DOCUMENTS

| | | |
|---|---|---|
| DE | 93 086 C | 7/1897 |
| EP | 0616797 B1 | 9/1994 |
| WO | WO96/07383 | 3/1996 |
| WO | WO96/23476 | 8/1996 |

OTHER PUBLICATIONS

PCT International Search Report PCT/US01/48798 dated Aug. 13, 2002.

* cited by examiner

Primary Examiner—Dennis Ruhl

(57) ABSTRACT

An applicator and method for delivering an object into a body cavity. In particular, the applicator includes a tubular insertion member having an outer surface, an inner surface, an insertion end, a first stop affixed to the inner surface proximate the insertion end, and a trailing end opposite the insertion end. The tubular insertion member containing a cage having an inner surface, an outer surface, a plurality of arms extending from an inner end portion toward the insertion end of the tubular insertion member, and a second stop affixed the outer surface proximate the inner end of the cage. The object is held within the cage until placement into the user's body and the first and second stops are capable of engaging to allow the object to be delivered into the body cavity while the cage remains constrained within the insertion member.

19 Claims, 4 Drawing Sheets

APPLICATOR FOR DELIVERING BULKY DEVICES

FIELD OF THE INVENTION

The present invention provides an applicator for inserting an object such as a bulky device into a human or other mammalian body cavity. In particular, the invention provides an applicator having a cage for holding a bulky device. Upon insertion, the bulky device is able to expand to its full size. Expulsion of the bulky device from the applicator requires substantially reduced force.

BACKGROUND OF THE INVENTION

Applicators for inserting and delivering objects into a body cavity typically include an insertion member having an insertion end and a trailing end opposite thereof, and an expulsion member slideably fitted within the insertion member. The trailing end will generally incorporate some sort of a gripping feature to allow a user to more or less securely hold the applicator during use, which may include the following steps: inserting the applicator into a body cavity, delivering a substantially enclosed object contained by the applicator, and withdrawing the applicator from the body.

Some catamenial devices such as tampons and collection cups may be bulky in size and may need to be compressed to fit within the applicator. These particular devices may be difficult to expel from the applicator. Expulsion often requires higher forces due to friction of the device against the inner surface of the insertion member.

Additionally, users of the push type applicators typically experience discomfort when inserting a tampon. Even though the outer surface of the insertion member may be smooth and somewhat lubricious for easy and smooth insertion, the tampon usually has a rough and irregular surface as a consequence of its absorptive and material properties. These properties tend to cause frictional discomfort when the tampon is expelled out of the insertion member and against the delicate walls and folds of the vagina.

Some applicators utilize a hollow tube having an open insertion end through which the tampon is always exposed while other applicators utilize a completely closed or partially closed design. The partially or completely closed insertion tip can help prevent premature contamination or wetting and subsequent expansion of the absorbent tampon. A tampon that has a portion expanded due to premature wetting will be difficult to remove from the applicator.

Examples of applicators having a protected insertion end are shown in U.S. Pat. Nos. 5,087,239; 5,279,541; 5,348,534 and 5,569,177. Additionally, these applicators are shown having segmented insertion portions with a hinge region or a reduced thickness in the insertion portion.

Attempts have been made to reduce the amount of force to expel tampon. In particular, WO 9607383 discloses an applicator having an insertion tip that has at least some of the paper fibers stretched and/or broken so as to allow it to be opened with a minimum amount of expulsion force. U.S. Pat. Nos. 4,923,440, 4,318,404 and 4,286,594 use a sheath or a portion of the insertion member that convolutes back onto itself to deliver the catamenial device to the vaginal cavity.

An attempt to provide an applicator for a bulky device is disclosed in EP 0 616 797. This publication discloses an insertion tube for a vaginal cup that has an outer tube slideable on an inner tube. At the insertion end of the inner tube, there are two jaws into which the vaginal cup is folded and placed. The outer tube is then moved up over the jaws to secure the cup within the applicator. After insertion of the applicator into the vaginal cavity, the outer tube is slid away from the jaws, which causes the jaws to open and release the vaginal cup.

Additionally, U.S. Pat. No. 6,095,998 discloses an expandable bag catamenial tampon and an applicator, which spreads the tampon open within the vaginal cavity. The bag-like tampon is placed over the leading end of the applicator in its initial flaccid configuration, which defines an initial width. The applicator is used to spread the tampon to a greater deployed width.

The present invention reduces the amount of friction between a bulky device such as a catamenial device and the applicator barrel as well as reducing the friction between the bulky device and vaginal wall. This is accomplished by having a cage for containing the catamenial device that slides out the applicator barrel (insertion member) and then glides the bulky device inside the vagina up to the predetermined point at which it opens up and to release the bulky device. The bulky device is then free to expand.

SUMMARY OF THE INVENTION

This invention relates to an applicator for delivering an object into a body cavity, the applicator including a tubular insertion member having an outer surface, an inner surface, an insertion end, a first stop affixed to the inner surface proximate the insertion end, and a trailing end opposite the insertion end. The tubular insertion member contains a cage having an inner surface, an outer surface, a plurality of arms extending from an inner end portion toward the insertion end of the tubular insertion member, and a second stop affixed the outer surface proximate the inner end of the cage. The object is held within the cage until placement into the user's body, and the first and second stops are capable of engaging to allow the object to be delivered into the body cavity while the cage remains constrained within the insertion member.

Additionally, this invention relates to a method of delivering an object into a body cavity from an applicator. The method includes the steps of inserting the insertion end of an insertable member into the user's body; displacing the cage contained therein toward the insertion end; and expelling an object from the cage into the body cavity.

DETAILED DESCRIPTION OF THE INVENTION

This invention relates to applicators for bulky devices. As used herein, the term "bulky device" generally refers to any type of device especially an intravaginal device such as an absorbent article, a support device, or an obstructing device useful to block the flow of and/or collect bodily liquids. The term includes, without limitation, all absorbent of tampons such as foam tampons, bag-type tampons, or compressed tampons; birth control devices such as diaphragms or intrauterine devices (IUDs); and incontinence devices and vaginal supports such as pessaries; and obstructing devices. Obstructing devices include menstrual collection cups and inflatable or expandable blocking devices.

Figure 1:
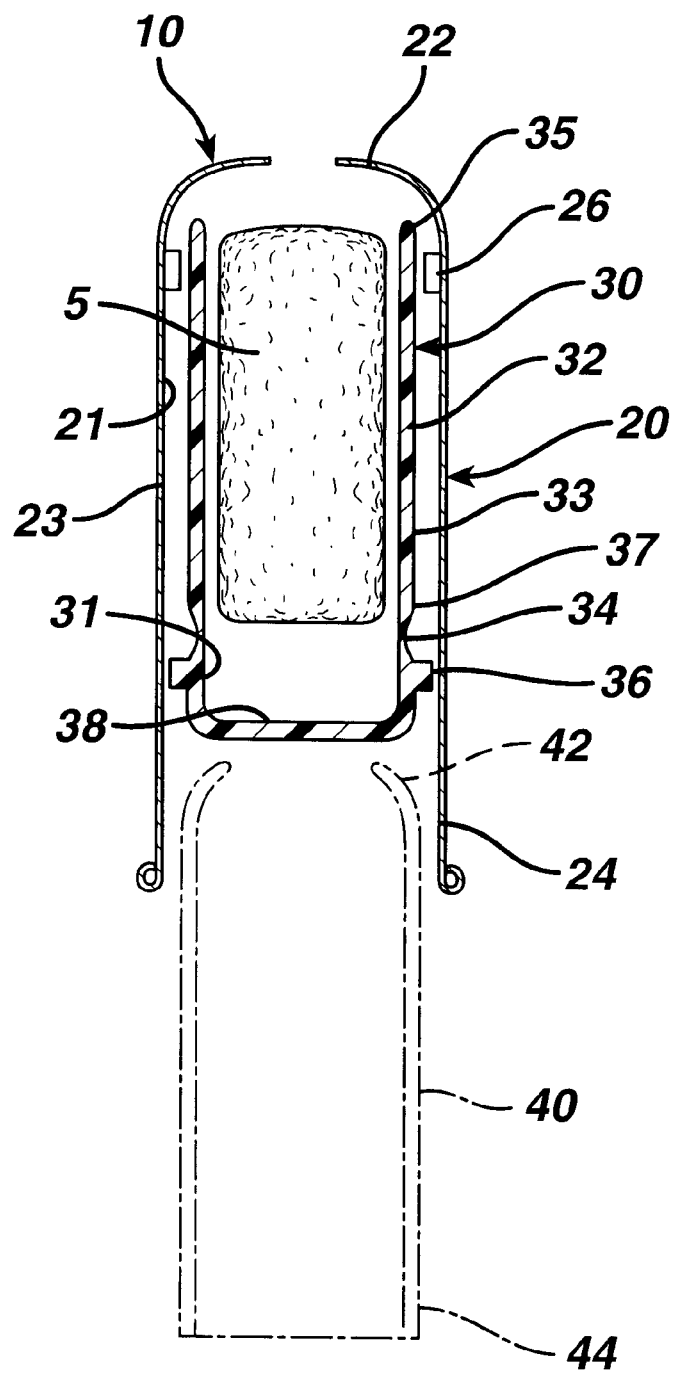
FIG. 1 is a cross-sectional view of an applicator containing a bulky device showing an optional plunger in phantom.

In a first embodiment shown in FIG. 1, applicator 10 has at least one tubular element, insertion member 20, cage 30. Additionally, applicator 10 may include an optional plunger 40 as shown in dotted lines. Insertion member 20 has insertion end 22, trailing end 24, inner surface 21, outer surface 23, and first stop 26 on inner surface 21. Insertion end 22 may be substantially closed, protecting bulky device 5 from wetness or contamination. Such closure may include a domed surface having cuts or perforations, pleats, segments pivotally attached to insertion end 22 (shown as closed petals 28 in FIG. 2), or other means. Cage 30 has inner surface 31, outer surface 33, at least one arm 32 (shown FIG. 2), resilient hinge 34, second stop 36, and end 38. In a preferred embodiment, cage 30 is a unitary unit but may be formed from multiple pieces integrally connected together. As used herein, a "unitary" device is one that has the characteristic of being a unit or a whole. This includes both devices that are created from a single element and those formed by fixing together individual elements to form the whole.

In the preferred embodiment, first stop 26 is disposed about the interior surface 21 of insertion member 20 and second stop 36 is disposed about the outer surface 33 of cage 30. It is preferred that at least one stop is a continuous ring.

Bulky device 5 is contained within cage 30 in a compressed form. Cage 30 may be any type of structure such as a closed or opened wall tube into which the bulky device is confined. In a preferred embodiment, the bulky device in contained within a plurality of extending arms. There are preferably at least two arms and more preferably, at least four arms. Arm 32 preferably includes a flexible, elongated structure such as a wide or narrow rod or tube. Arm 32 may have a flat, cylindrical or curved shape with preferably a smooth, convexly rounded outer surface to provide a comfortable structure for contacting the user's body. Arm 32 has first end 35 and second end 37. First end 35 is adjacent the insertion end 22 of the insertion member 20 and second end 37 is adjacent hinge 34. First end 35 may include a straight, blunt end or may include a hook-like end that encases the outer end of bulky device 5.

As shown in FIG. 1, plunger 40 has pushing end 42 and trailing end 44. Plunger 40 is slideably fitted within the trailing end 24 of insertion member 20. Pushing end 42 has means such that cage end 38 is pushed toward insertion end 22 of insertion member 20. For instance, pushing end 42 may have a smaller inner circumference than cage end 38. While plunger 40 has been illustrated as a tubular member, alternate embodiments may be use. For example, a stick-type of pusher or a solid implement may be used to push cage end 38 toward insertion end 22. Alternately, the user may digitally push cage end 38 toward insertion end 22. In this embodiment, the user's finger would replace the use of a tubular plunger 40. Plunger 40 can be a separate element from cage 40, or it may be removably attached thereto. Additionally, plunger 40 may be unitary with the cage 30.

First stop 26 engages second stop 36 to prevent complete expulsion of cage 30 from insertion member 20. First stop 26 and second stop 36 are configured so as when cage 30 is fully delivered from insertion member 20, hinge 34 is aligned with petals 28. Additionally, first stop 26 can also serve to reduce the inner diameter of insertion member 20 to better maintain cage 30 in a closed arrangement until fully deployed.

Although it is not required, applicator 10 may have fingergrip-enhancing features disposed on trailing end 24 of insertion member 20.

Figure 2:
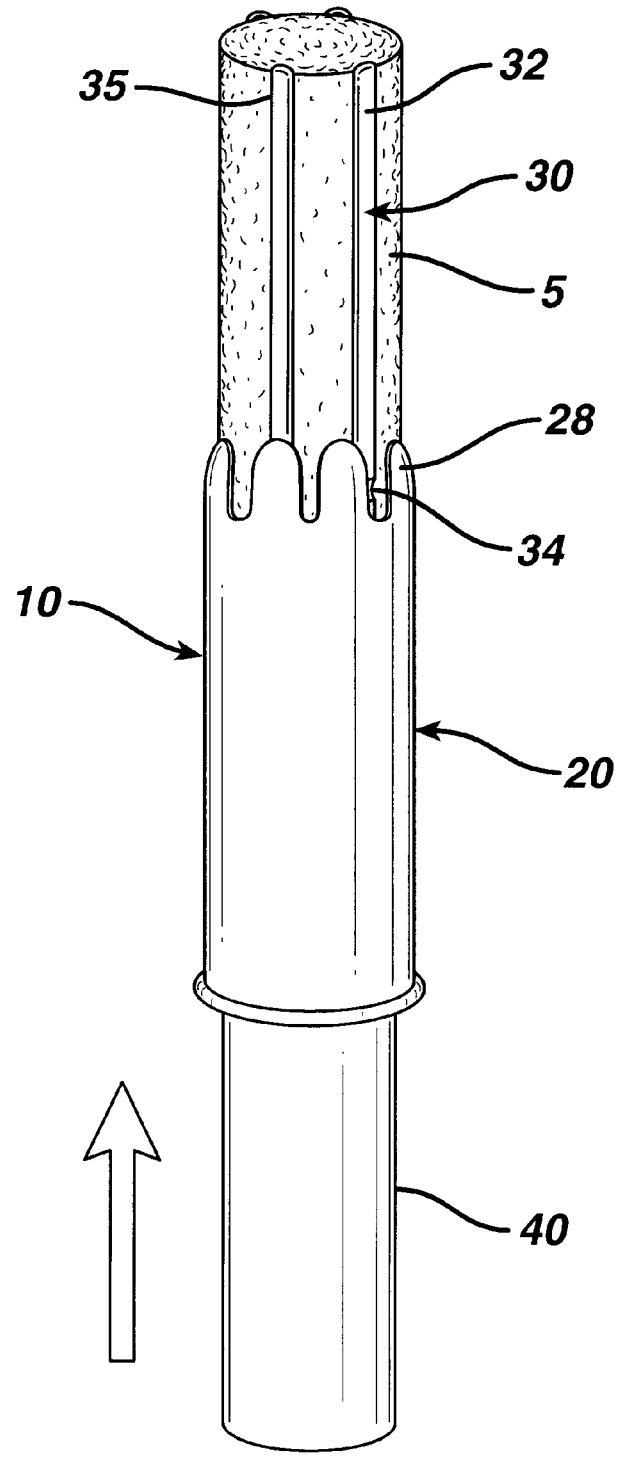
FIG. 2 is a plan view of the applicator of FIG. 1 with the bulky device partially expelled.

FIG. 2 shows cage 30 partially expelled from insertion member 20. To achieve this state, plunger 40 has been pushed toward insertion end 22, causing cage 30 to open petals 28. In a preferred embodiment, arm 32 slides on inner surface 21 of insertion member 20 and on first stop 26. At the point of expulsion as illustrated in FIG. 2, resilient hinge 34 has not been deployed and bulky device 5 is still compressed, maintaining its form within arms 32 of cage 30.

Figure 3:
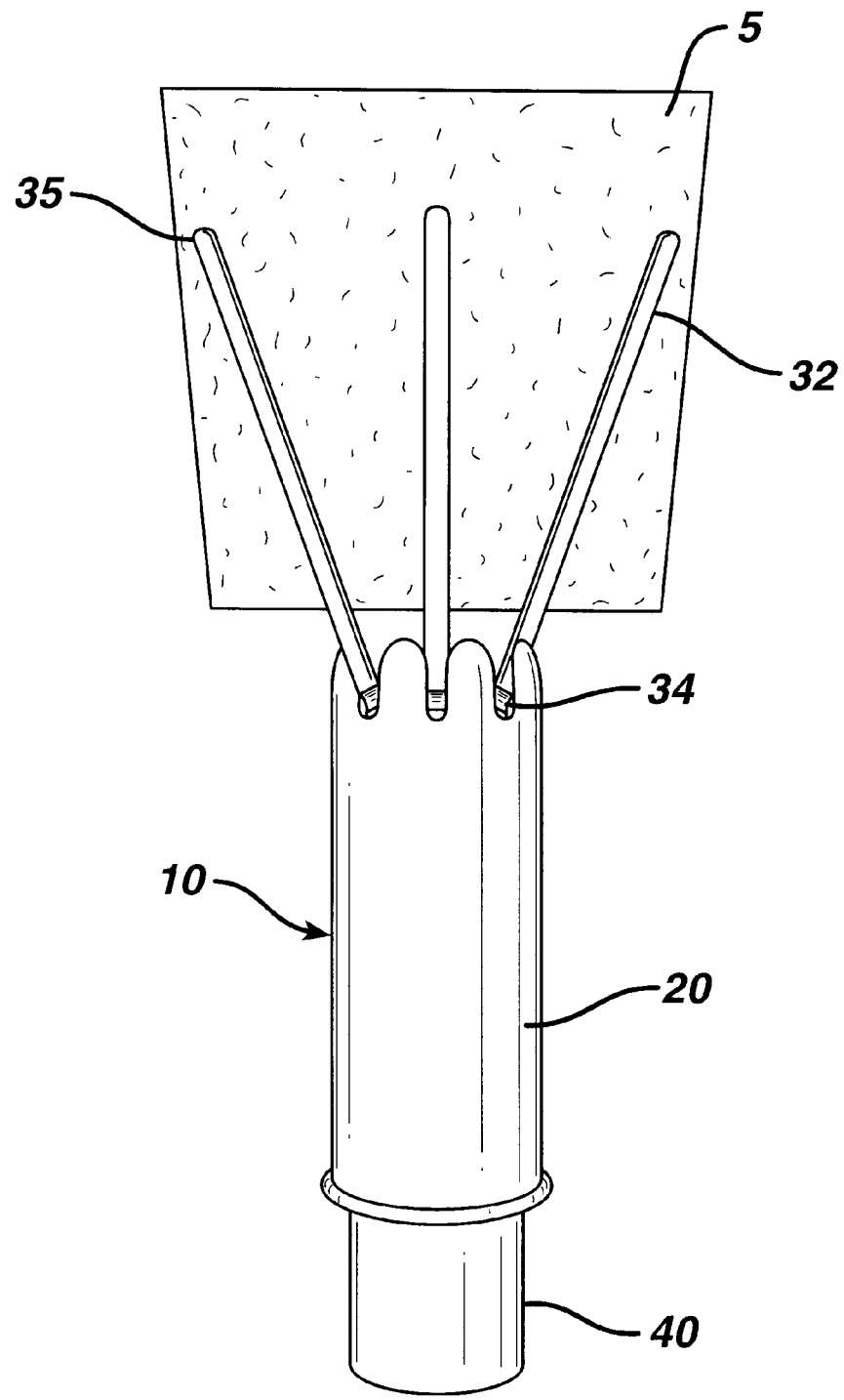
FIG. 3 is a plan view of the applicator of FIG. 1 with the bulky device expelled and the cage fully deployed.

FIG. 3 shows arms 32 completely expelled and bulky device 5 in a fully expanded state. First stop 26 contacts second stop 36 and resilient hinge 34 is deployed. As resilient hinge 34 is deployed, arms 32 open and release bulky device 5 from cage 30.

In use, a woman may place insertion end 22 into the vaginal opening, delivering bulky device 5 into the vagina by pushing on plunger 40 until bulky device 5 is expelled from cage 30 and withdrawing applicator 10 from the body, leaving bulky device 5 within the vagina.

Alternately, a user could pull insertion member 20 onto plunger 40 while maintaining plunger 40 steady relative the user's body. This substantially eliminates friction between the bulky device 5 and the user's body.

Figure 4:
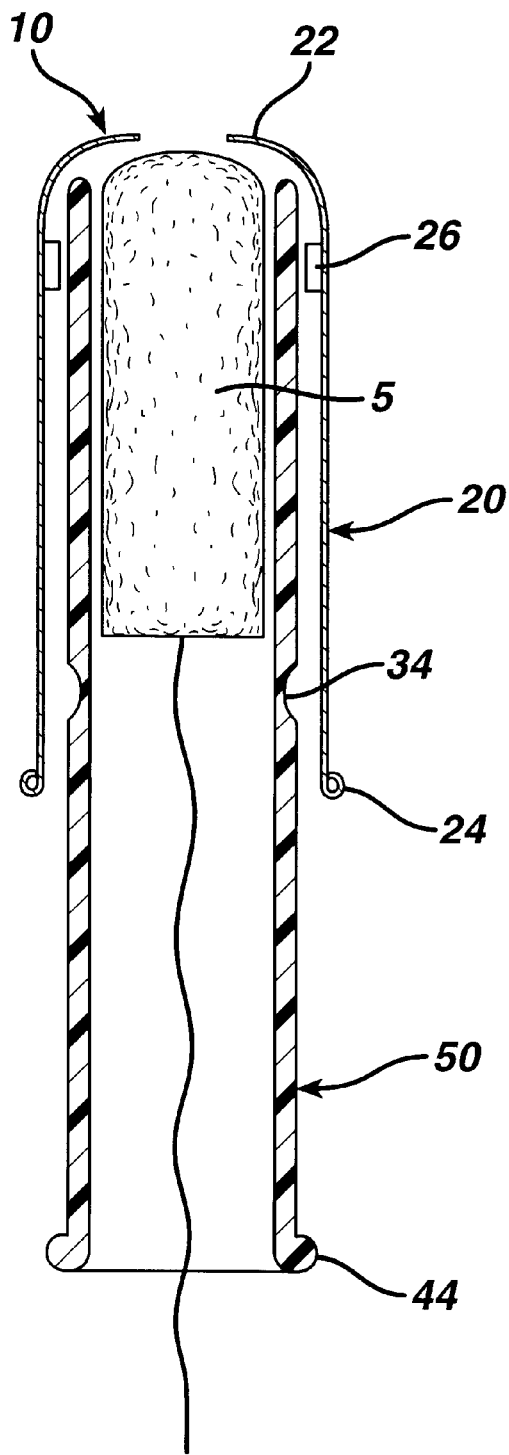
FIG. 4 is an alternate embodiment of an applicator containing a bulky device.

FIG. 4 shows an alternate embodiment of the invention. Applicator 10 has insertion member 20 and a unitary cage/plunger combination 50. Bulky device 5 is contained within cage/plunger combination 50. Cage/plunger combination 50 is pushed toward the insertion end 22 of insertion member 20 until trailing end 44 contacts trailing end 24 of insertion member 20. Resilient hinge 34 deploys and bulky device 5 is delivered into the vaginal cavity. Alternately, a third stopper may be included on cage/plunger 50 to contact first stop 26.

Applicators are generally constructed of one of two basic materials: plastic and paperboard. Paperboard products appeal to both the manufacturer and the consumer, derived from factors such as ease of manufacture, cost of manufacture, purchase cost, environmental benefits, and flushability. A gripping member, manufactured separately, can be retrofitted onto a paperboard tubular insertion member, without significantly eliminating any of the noted appeal.

The cardboard used in tampon applicators can be a single layer of cardboard material, or it can be a plurality of laminated layers to provide multiple benefits relating to the various layers. Useful cardboard stock for the formation of the tubular elements includes, without limitation, paperboard, cardboard, cup stock, paper, and the like. The laminated cardboard material may include a surface layer or coating of plastic, wax, silicone, and the like, which may be useful to increase the comfort to the user during insertion and withdrawal. The plastic coating may include, without limitation, polyolefins such as polyethylene and polypropylene, polyesters such as polyethylene terephthalate, polycaprolactone, polyvinyl alcohol, ethylene-vinyl acetate copolymers, cellophane, and the like.

Preferred tubular element materials include laminated cardboard. Preferred laminated cardboard includes plastic laminated or plastic coated cardboard materials. These plastic laminated cardboard materials may include additional layers such as adhesive layers, tie layers, and the like.

Examples of processes used for making paperboard applicator components are as follows: spiral winding as disclosed in U.S. Pat. No. 5,346,468; convolute winding as disclosed in U.S. Pat. No. 4,508,531; and forming a sheet around a mandrel and then sealing an overlapped seam as disclosed in U.S. Pat. Nos. 4,755,164 and 5,599,293.

The applicator and cage may also be manufactured from conventional plastic, such as injection-moldable or blow-moldable plastic, biodegradable plastic, such as those disclosed in the commonly assigned application U.S. Ser. No. 08/006,013 (Dabi et al. filed Jan. 15, 1993, the entire contents herewith incorporated by reference). All commercially available products are made from an olefin-based polymer, such as polyethylene. It is preferred that the insertion members be formed through an injection molding process. This process is used because the manufacture must balance some key characteristics of the tubular insertion member. Molding inserts and cores are machined to form a tapered product, such that the wall thickness in the gripping region is relatively thick to maintain structural stability during the insertion and expulsion steps of use, while the thickness in the insertion end is minimized to provide flexibility and low expulsion force. Injection molding also enables the manufacture to make uniquely shaped tubular insertion members. There are less sophisticated/ expensive polymer forming techniques, such as extrusion and blow molding that can be employed. Manufacturing a gripping member separately, and then retrofitting it to the insertion member, allows these alternatives to be used. Preferably the cage is made from a material that has a low friction coefficient against the applicator and allows for easy movement with little resistance. Additionally, the arms of the cage must be flexible thereby allowing the arms to pivotally open and release the bulky device.

EXAMPLES

The present invention will be further understood by reference to the following specific Examples that are illustrative of the composition, form and method of producing the device of the present invention. It is to be understood that many variations of composition, form and method of producing the device would be apparent to those skilled in the art. The following Examples, wherein parts and percentages are by weight unless otherwise indicated, are only illustrative.

Example 1

A commercially available plastic applicator was manually loaded with a Beppy foam tampon (available from Asha International, Rotterdam). The Beppy tampon is approximately 47 mm in diameter, measured in an uncompressed state. A similar tampon was loaded into a plastic prototype of the present invention. The two applicators were then hand tested for expulsion force by gripping the barrel finger grip with a stand that would not force on the section of the barrel but provide strength in the longitudinal direction. The applicator, gripped in this way, was forced by hand against a digital/top loading balance and the peak of resisting force for the expulsion of the tampon was visualized and recorded. Each sample was tested ten times and the results averaged. The averages are reported in Table 1.

| Sample | Force Required |
|---|---|
| Commercial product | 1845 g |
| Present Invention | 1075 g |

It is clear from this data that the use of the cage in the applicator of the present invention significantly reduces the force necessary to expel a resilient, otherwise unrestrained, product in comparison to a conventional applicator.

The specification and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. An applicator for delivering an object into a body cavity, said applicator comprising a tubular insertion member having an outer surface, an inner surface, an insertion end, a first stop affixed to said inner surface proximate said insertion end, and a trailing end opposite said insertion end, said tubular insertion member containing a cage having an inner surface, an outer surface, a plurality of arms extending from an inner end portion toward said insertion end of said tubular insertion member, a second stop affixed said outer surface proximate said inner end of said cage, wherein said object is held within said cage until placement into the user's body and said first and second stops are capable of engaging to allow said object to be delivered into said body cavity while said cage remains constrained within said insertion member.

2. An applicator of claim 1, wherein said cage comprises at least 4 arms.

3. An applicator of claim 1, wherein each arm is operatively associated with at least one resilient hinge proximate said end to permit said arm to flex to an open position thereby releasing said object from said cage.

4. An applicator of claim 1, wherein said insertion member is substantially closed at said insertion end to protect said object from contamination prior to expulsion.

5. An applicator of claim 1, wherein said insertion end comprises a domed insertion end having inwardly directed petals.

6. An applicator of claim 1, wherein said object is a bulky device selected from the group consisting of absorbent articles, incontinence devices, obstructing devices, and birth control devices.

7. An applicator of claim 6, wherein said absorbent article is an absorbent catamenial tampon.

8. An applicator of claim 7, wherein said absorbent catamenial tampon is a bag-type tampon.

9. An applicator of claim 7, wherein said absorbent catamenial tampon is a foam tampon.

10. An applicator of claim 6, wherein said obstructing device is a collection cup or an expandable blocking device.

11. An applicator of claim 10, wherein said collection cup is a menstrual collection cup.

12. An applicator of claim 6, wherein said incontinence device is a pessary.

13. An applicator of claim 6, wherein said birth control device is a diaphragm or an intrauterine device.

14. An applicator of claim 1, further comprising a plunger.

15. An applicator of claim 14, wherein said plunger is unitary with said cage.

16. A method of delivering an object into a body cavity from an applicator, said applicator including a tubular insertion member having an outer surface, an inner surface, an insertion end and a trailing end opposite said insertion end, said tubular insertion member contacting a cage having an inner surface, an outer surface, and a plurality of arms extending from an inner end portion toward said insertion end of said tubular insertion member, said object being held within said cage, said method comprising the steps of:

a) inserting said insertion end into the user's body;

b) displacing said cage containing said object toward said insertion end; and c) expelling said object from said cage into said body cavity.

17. A method of claim 16, further comprising said plurality of arms to flex at at least one resilient hinge proximate said end to release said object into said body cavity.

18. A method of claim 16, further comprising the step of engaging a first stop affixed to said inner surface of said tubular insertion member proximate the insertion end and a second stop affixed to said outer surface of said cage proximate said inner end, wherein said object is held within said cage until placement into the user's body and said first and second stops are capable of engaging to allow said object to be delivered into said body cavity while said cage remains constrained within said insertion member.

19. A method of claim 16, further comprising the step of engaging the end of said cage with a plunger to move said cage toward said insertion end.

* * * * *